US00PP33284P2

(12) United States Plant Patent
Bagdasarian et al.

(10) Patent No.: US PP33,284 P2
(45) Date of Patent: Jul. 27, 2021

(54) STRAWBERRY PLANT NAMED 'SIERRA'

(50) Latin Name: ***Fragaria* x *ananassa***
Varietal Denomination: Sierra

(71) Applicants: Jimmy Haig Bagdasarian, Santa Cruz, CA (US); Nicholas Jack Pinkerton, Redding, CA (US); Travis Stegmeir, Salinas, CA (US)

(72) Inventors: Jimmy Haig Bagdasarian, Santa Cruz, CA (US); Nicholas Jack Pinkerton, Redding, CA (US); Travis Stegmeir, Salinas, CA (US)

(73) Assignee: Lassen Canyon Nursery, Inc., Redding, CA (US)

( * ) Notice: Subject to any disclaimer, the term of this patent is extended or adjusted under 35 U.S.C. 154(b) by 0 days.

(21) Appl. No.: 17/063,716

(22) Filed: Oct. 5, 2020

(51) Int. Cl.
*A01H 5/08* (2018.01)
*A01H 6/74* (2018.01)

(52) U.S. Cl.
USPC ..... Plt./208

(58) Field of Classification Search
USPC ..... Plt./208
See application file for complete search history.

(56) References Cited

U.S. PATENT DOCUMENTS

| | | | |
|---|---|---|---|
| PP22,473 | P2 | 1/2012 | Bagdasarian |
| PP26,974 | P3 | 7/2016 | Bagdasarian |
| PP27,034 | P3 | 8/2016 | Bagdasarian |
| PP27,190 | P3 | 9/2016 | Bagdasarian |
| PP30,326 | P2 | 4/2019 | Bagdasarian |
| PP30,426 | P2 | 4/2019 | Bagdasarian |
| PP30,427 | P2 | 4/2019 | Bagdasarian |

*Primary Examiner* — Annette H Para
(74) *Attorney, Agent, or Firm* — Phase M Legal

(57) ABSTRACT

A new and distinct variety of strawberry plant (*Fragaria* x *ananassa*) named 'Sierra' is presented here. This new short-day strawberry variety is characterized by moderate vigor plants which produce attractive conical fruit, with a sweet strawberry flavor, and a desirable lighter red exterior color making it market attractive. The fruit of 'Sierra' ripens nearly up to the calyx and there is no unripe shoulder. In addition, the variety is fully remontant in cool coastal areas of California, producing high quality fruit all season long.

7 Drawing Sheets

Latin name of the genus and species of the plant claimed: Botanical classification: *Fragaria* x *ananassa.*

Variety denomination: The new strawberry variety denomination is 'Sierra'.

BACKGROUND OF THE INVENTION

Field of Invention

The present invention relates to a new and distinct variety of strawberry named 'Sierra.' This new short-day strawberry variety is the result of a controlled cross in an ongoing breeding program made in 2013. Jimmy Bagdasarian, Nicholas Pinkerton and Travis Stegmeir are the co-inventors. The variety is botanically known as *Fragaria* x *ananassa.*

The primary market for the 'Sierra' variety is for fresh market sales of the fruit. 'Sierra' produces attractive, high quality, large firm berries, which have good flavor. The berries produced by 'Sierra' are relatively early fruiting, enabling growers to capture early market windows.

Comparison with Parent Varieties

The new variety 'Sierra' resulted from a controlled cross conducted in an ongoing breeding program between a strawberry variety designated 'Lucia,' (U.S. Plant Pat. No. 26,974) and a strawberry variety designated 'Emilia,' (U.S. Plant Pat. No. 30,427). The female parent, 'Lucia,' is a short-day variety characterized by a vigorous plant, and highly uniform, light colored conical fruit. The fruit has an exceptional flavor, and 'Lucia' is considered fully remontant in coastal areas of cooler temperatures. The male pollen parent 'Emilia' is also a short-day plant, characterized by its large, firm, long, conical to wedge shaped fruit which have a light red exterior and interior color. Plants of 'Emilia' show high vigor and are considered remontant in cooler coastal regions.

The aforementioned controlled cross was carried out in a breeding program at Santa Cruz, Calif., USA. Pollen taken from an 'Emilia' plant pollinated a female 'Lucia' plant. The flowers were covered so that no other pollen could contaminate the procedure.

Strawberries developed, were later harvested and the seeds resulting from this cross were extracted and germinated in a greenhouse at Redding, Calif., USA. The resulting seedlings were then transplanted to Shastina, Calif. in 2014, grown for an additional period and allowed to propagate asexually via stolens. Plants were then harvested and planted in breeding test plots in early to mid-October in Oxnard, Calif. (Ventura County), and Watsonville, Calif. (Monterey County). The selection of the new variety was first made in Oxnard, Calif., and designated '8R58' in 2014. This selection was later named 'Sierra.'

The new variety was further propagated asexually by stolens in breeding plots in: Macdoel, Calif. (Siskiyou County); and Manteca, Calif. (San Joaquin County). The new variety has also been "meristemed." Small pieces of plant material (approximately 0.5 mm in diameter), consisting of the undifferentiated meristem tissue and one or two leaf primordia, were removed from the buds on crowns of young daughter plants, then placed on nutrient medium, and new plants were grown from them. Planting stock from the "meristemed" plants were grown in a screenhouse located in Redding, Calif.

The propagules of 'Sierra' are identical to the original plant in all distinguishing characteristics; accordingly, the propagation has demonstrated that the traits disclosed herein remain fixed and true to type through successive generations of asexual reproduction.

SUMMARY OF THE INVENTION

'Sierra' is a short-day variety exhibiting the following combination of characteristics, which have been observed repeatedly, and which distinguish this strawberry plant as a new and distinct variety:

1. The variety produces large sized fruit;
2. The fruit is well shaped conical;
3. The fruit is attractive, having a glossy light red exterior and interior;
4. The fruit is sweet tasting, with good flavor;
5. The variety produces a high volume of marketable fruit;
6. The plants of the variety maintain a semi-open architecture; and,
7. The variety is fully remontant in a cool, coastal environment.

'Sierra' fruit demonstrates characteristics and qualities that are desired by fresh market strawberry sales companies. The lighter, red color is preferred by many shippers of fresh strawberries, as the darker berries are more likely to be viewed as overripe by buyers are lighter colored berries. 'Sierra' is also a firm berry, which should lend well to a fresh market where shipping is a major factor. The vigor and density of 'Sierra' plants are moderate, with flowers that extend slightly over the canopy, allowing for adequate pollination. Fruit are easily seen and accessible on the shoulders of the beds allowing for ease of picking. This moderate vigor and slightly open canopy hold an advantage over dense canopies in that spray coverage can penetrate more efficiently over denser varieties.

BRIEF DESCRIPTION OF THE DRAWINGS

The accompanying color photographs, identified as FIGS. 1 through 7, show the appearance of typical specimens of the new strawberry variety, initially designated '8R58,' and now named 'Sierra.' These Figures depict the colors, as nearly true as it is reasonably possible given differences in color illustrations of this character. Accordingly, color in the photographs may differ slightly from the colors discussed in the botanical description. The photographs of the depicted plant, plant parts, and fruit of 'Sierra' were taken in May 2020.

DETAILED BOTANICAL DESCRIPTION OF THE PLANT

Figure 1:
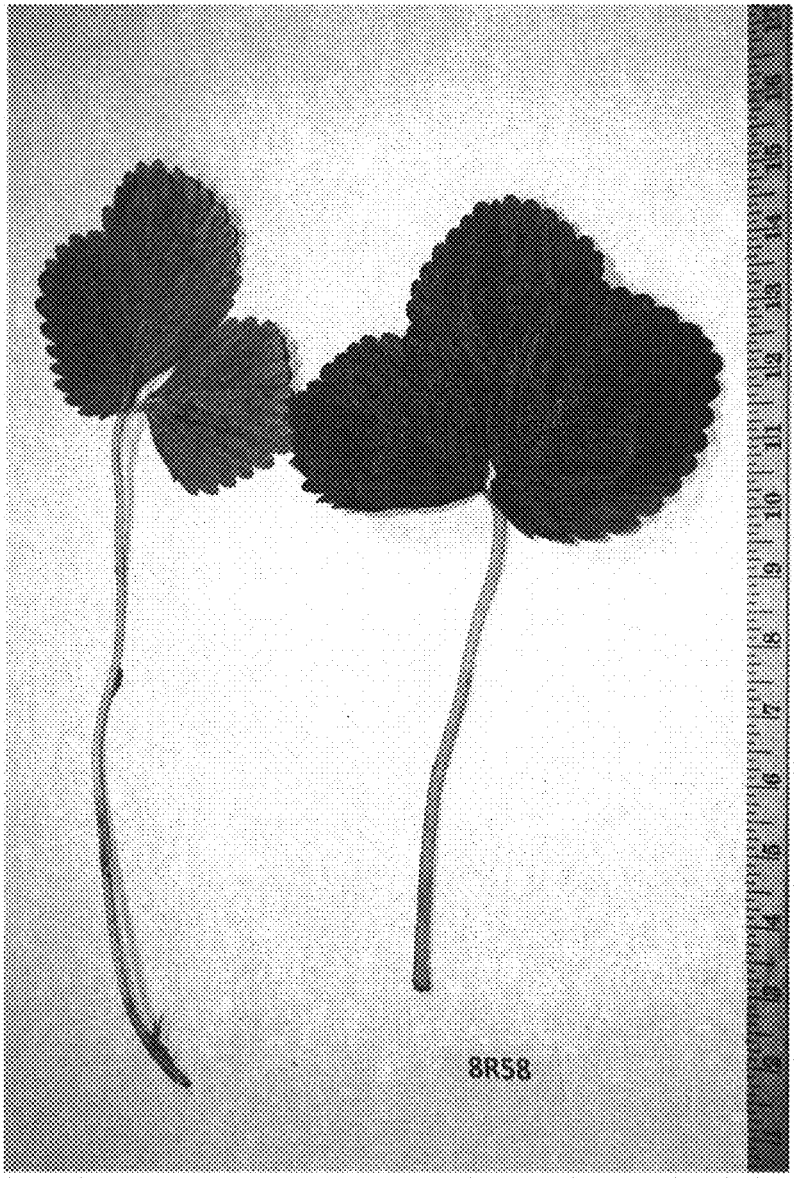
FIG. 1 shows typical leaf and petiole structure at mid-season.
Figure 2:
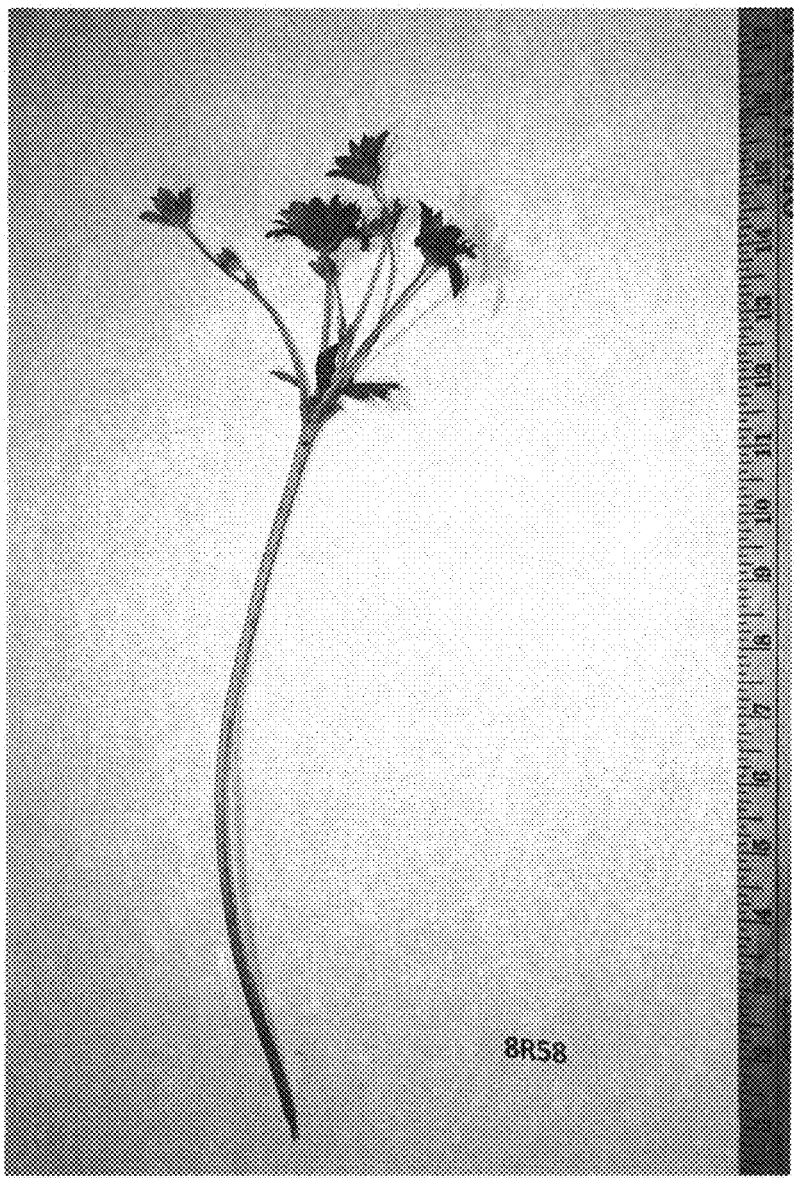
FIG. 2 shows an inflorescence at mid-season.
Figure 3:
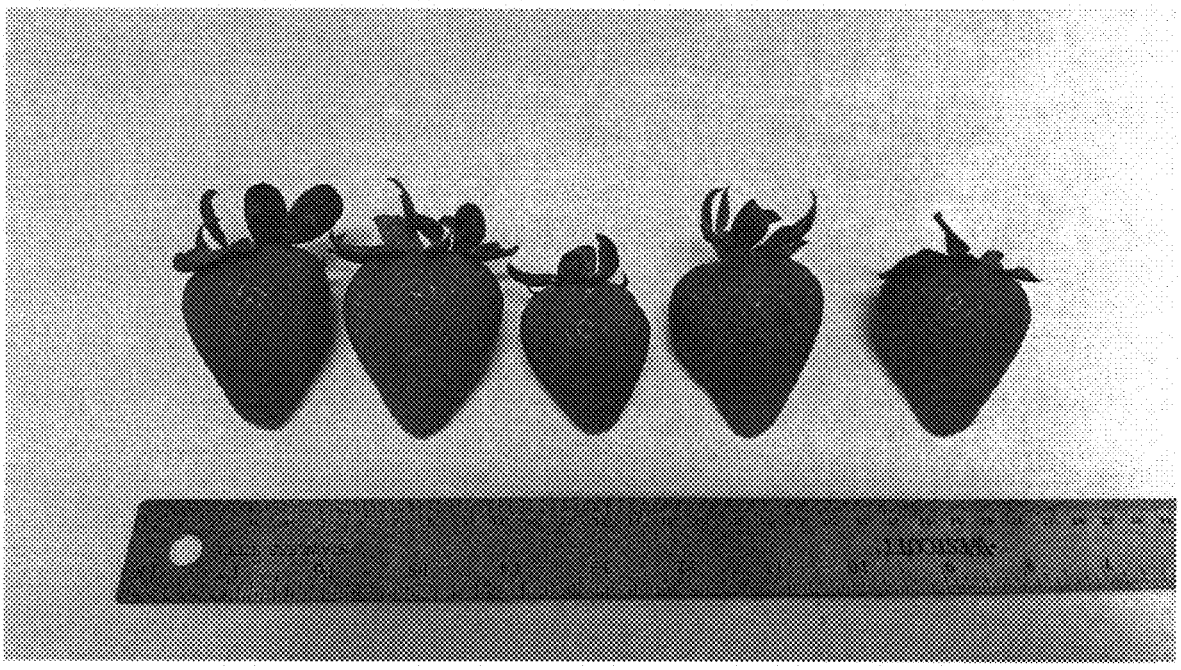
FIG. 3 shows a selection of typical mid-season fruit.
Figure 4:
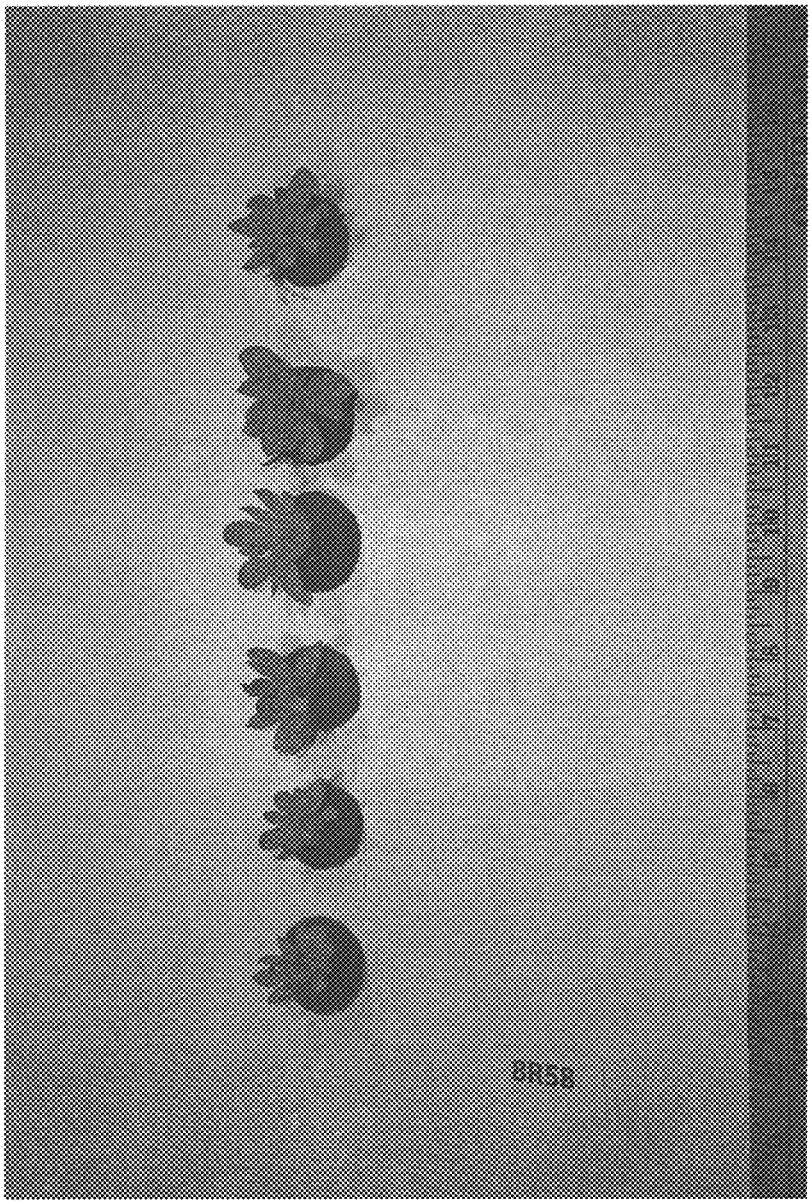
FIG. 4 shows typical calyx position over the berry of 'Sierra'.
Figure 5:
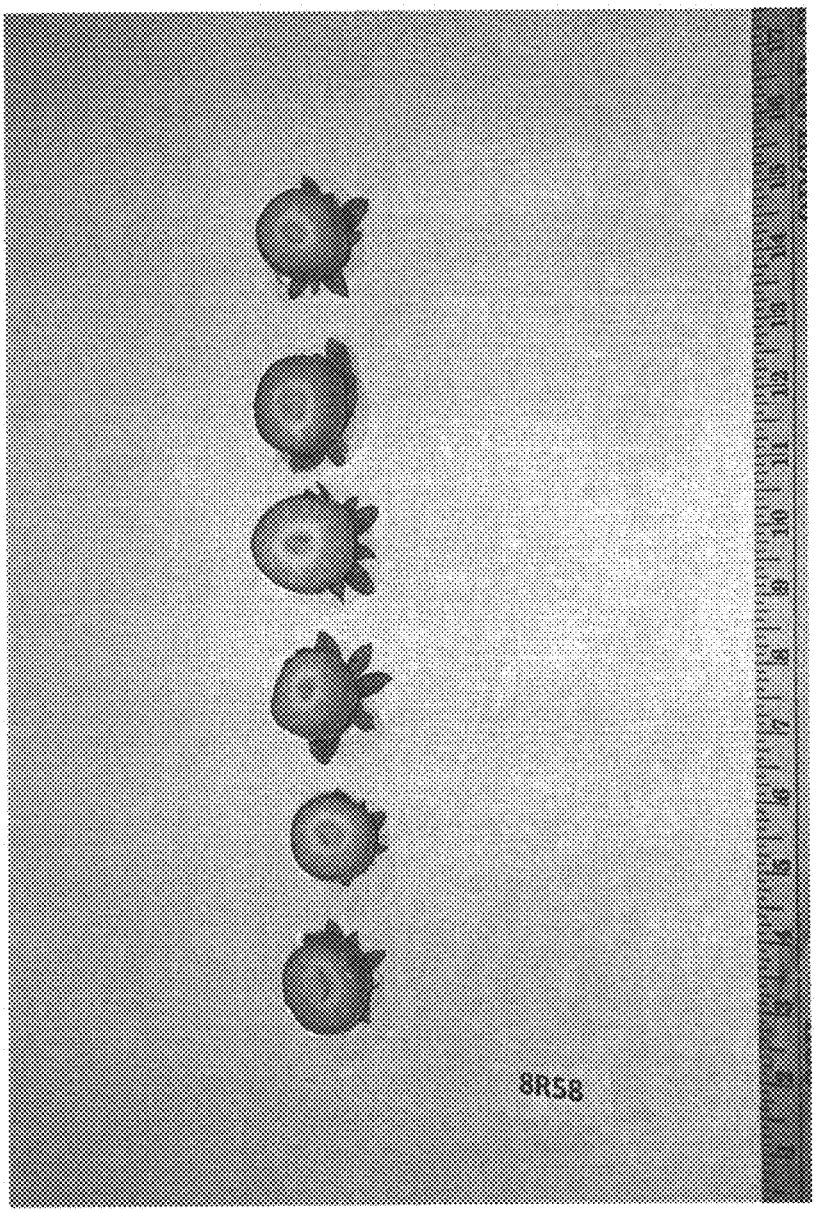
FIG. 5 shows a cross-section of typical fruit internal coloration and core size.
Figure 6:
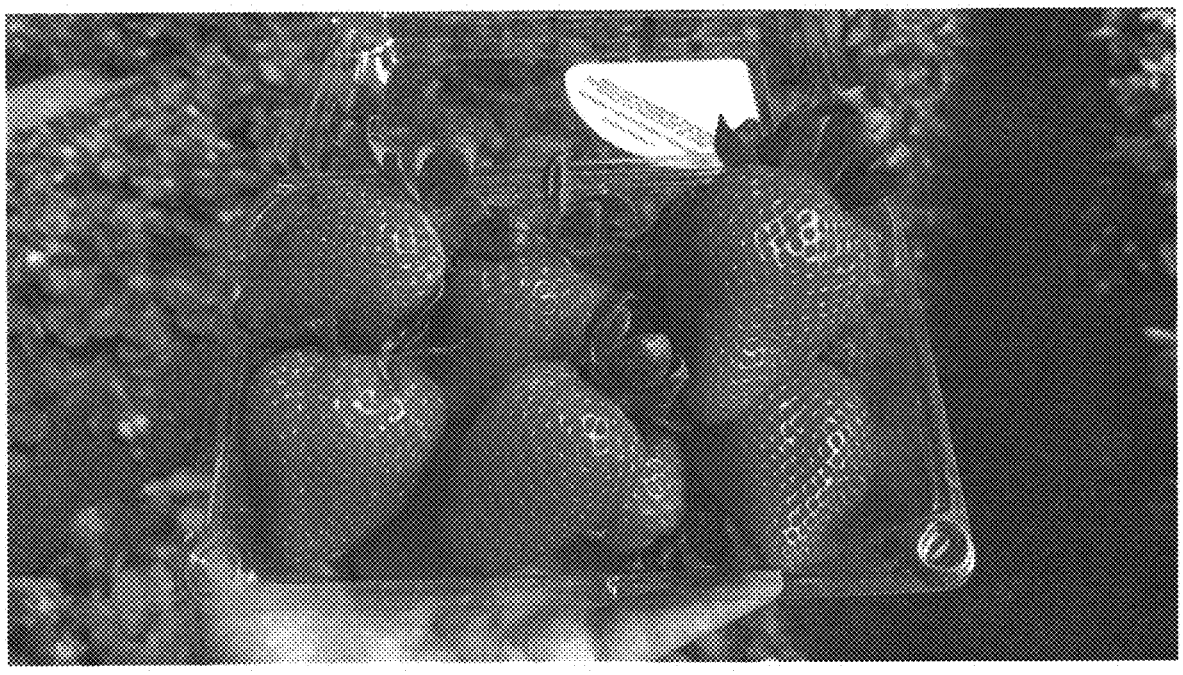
FIG. 6 shows a container of freshly picked fruit.
Figure 7:
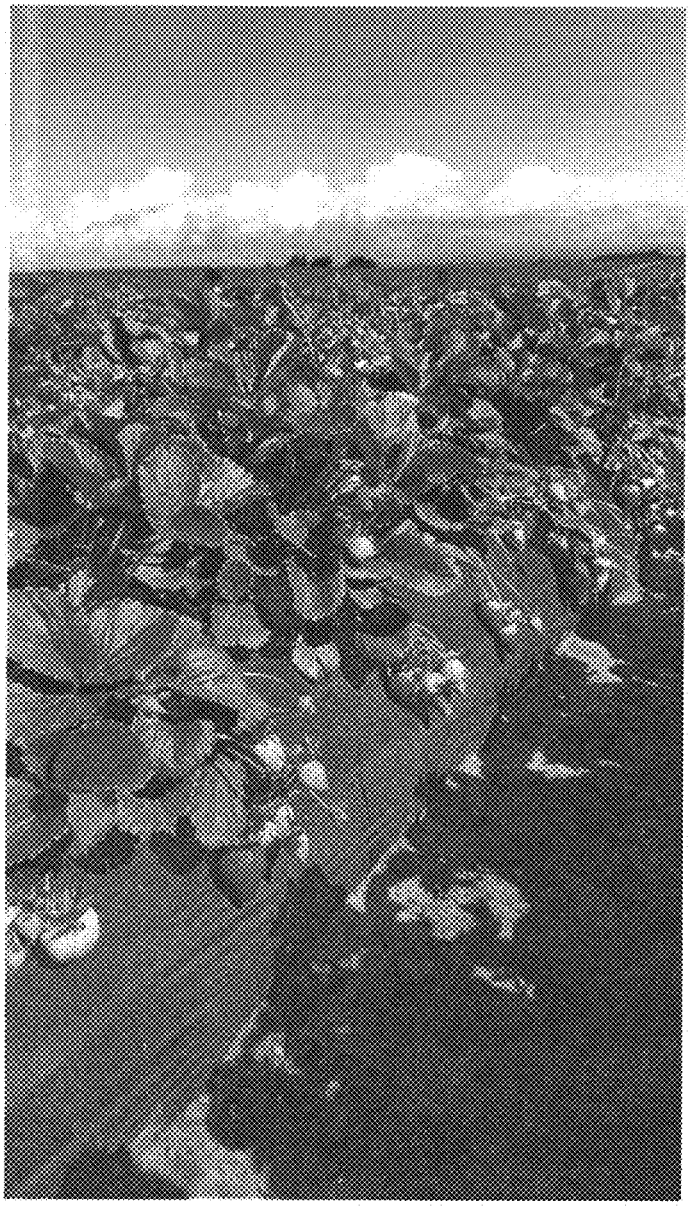
FIG. 7 shows typical plants in a field and position of ripe fruit on the shoulder.

'Sierra' is a new and distinct variety of strawberry, genus and species *Fragaria* x *ananassa*. It is the result of a cross between its female parent, 'Lucia' (U.S. Plant Pat. No. 26,974), and its male parent 'Emilia' (U.S. Plant Pat. No. 30,427). 'Lucia' and 'Emilia' are both short-day varieties which are both remontant in coastal environments. 'Sierra' is also a short-day variety that has remontant or ever-bearing tendencies in temperate coastal environments and is partially remontant in warmer inland environments like its parents. Plants of 'Sierra' bloom only once in our high elevation nursery, and do not bloom in the heat of our low elevation nursery location in Manteca, Calif., consistent with other short-day varieties. The plants of the new variety have a moderate vigor and produce multiple crowns during the growing season. 'Sierra' exhibits several characteristics which are improvements over one or both of its parent varieties, and other known cultivars. The characteristics of 'Sierra' were observed in plants aged about 6 months from planting. These characteristics and comparisons with other cultivars are discussed following.

The fruit size of 'Sierra' is large, slightly larger than its 'Lucia' parent, and similar in size, but better in shape than its other parent 'Emilia.' The size of fruit of 'Sierra' is ideal where it is not too large where it could be damaged in containers, but not too small to allow for efficient picking and packing. The fruit of 'Sierra' also hangs down on the shoulder of the bed to allow for highly visible fruit and ease of picking.

'Emilia,' produces long conic fruit, while the fruit of 'Sierra' is mostly conical. The fruit of 'Sierra' generally ripens evenly from the tip to the shoulders of the berry, resulting in a uniform light red color over the whole fruit. In contrast, the fruit of 'Emilia' has a pronounced tip to top ripening pattern. The fruit of 'Sierra' is mostly absent of creases and is generally smooth, and has a firmness that is between its two parents, where it is slightly firmer than 'Lucia,' and on par or slightly less firm than 'Emilia'.

The data set forth for 'Sierra' in Tables 1, 2, and 3 was collected in May 2020 from plants grown at a test plot in Moss Landing, Monterey County, Calif. Color terminology where noted herein is in accordance with the Pantone Color Formula Guide GP 1201.

In Table 1, the observed characteristics of 'Sierra' are set forth.

TABLE 1

Detailed Description of Characteristics of 'Sierra'

| | | |
|---|---|---|
| SPECIFICATION: | Genus/Species | *Fragaria* X *ananassa* |
| | Market Name | Strawberry |
| PARENTS: | Female | 'Lucia' (U.S. Plant Pat. No. 26,974) |
| | Male | 'Emilia' (U.S. Plant Pat. No. 30,427) |
| PLANT: | Type | Short Day |
| | Growth Habit | Semi-upright |
| | Foliage density | Moderate |
| | Vigor | Moderate |
| | Height | Average 35.2 cm; range 30 cm to 41 cm |
| | Width | Average 51.1 cm; range 40 cm to 60 cm |
| | Crowns | Multiple crowns produced throughout season |
| | Disease tolerance | Test plots have shown tolerance to *Fusarium* and *Verticillium* wilt |
| LEAF: | Width | Average 35.2 cm; range 26.5 cm to 38.5 cm |
| | Color | Adaxial surface: Pantone 371 C<br>Abaxial surface: Pantone 7490 U |
| | Pubescens | Mediu density |
| | Inter-vein blistering | Slight |
| | Glossiness | Slight |
| | Variegation | None |

TABLE 1-continued

| Detailed Description of Characteristics of 'Sierra' | | |
|---|---|---|
| TERMINAL LEAFLET: | Length | Average 91.2 mm; range 85 mm to 100 mm |
| | Width | Average 79.7 mm; range 66 mm to 88 mm |
| | Ratio Length to width | 1.14 |
| | Margins | Serrate to crenate |
| | Leaf shape | Obovate to orbicular |
| | Base shape | Rounded to cuneate |
| | Cross-section shape | Slight concave to slight convex |
| PETIOLE: | Pubescens | Medium density |
| | Petiole color | Pantone 381 U |
| | Petiole length | Average 26.6 cm; range 19.9 cm to 30 cm |
| | Petiole diameter | Average 4.34 mm; range 3.46 mm to 5.08 mm |
| STIPULE: | Anthocyanin coloration | Slight |
| | Length | Average 19 mm; range 16.14 mm to 21.63 mm |
| | Width | Average 10.9 mm; range 7.15 mm to 12.79 mm |
| STOLEN: | Anthocyanin coloration | Weak, but present |
| | Pubescens | Moderate, fine |
| | Diameter | Average 3.55 mm; range 2.93 mm to 4.39 mm |
| INFLORESCENCE: | Flowering time | Moderately early |
| | Position | At or slightly above the canopy |
| | Number of blooms | Average 6; range 4 to 10 |
| | Length | Average 38 cm; range 32.5 cm to 44 cm |
| | Flower diameter | Average 28.7 mm; range 17.8 mm to 34.1 mm |
| | Petal arrangement | Slightly overlapping |
| | Petal number | Average 5.6; range 5 to 7 |
| | Petal length | Average 12.9 mm; range 8.31 mm to 15.54 mm |
| | Petal width | Average 11.8 mm; range 8.78 mm to 14.67 mm |
| | Ratio Length to width | 1.09 |
| | Petal color | Pantone 11-4300 TPX |
| | Calyx | Slightly larger than the corolla |
| | Calyx color | Adaxial Pantone 370 U<br>Abaxial Pantone 392 U |
| | Stamens | Average 25.8; range 20 to 30 |
| | Pedicel | Attitude of hairs is upright |
| FRUIT: | Bearing | Short day, but remontant in cool coastal climates |
| | Shape | Conic |
| | Size | Seasonal average: 32 g |
| | Achenes | At or slightly below fruit surface |
| | Glossiness | Medium high |
| | External color | Pantone 185 C |
| | Internal color | Pantone 032 U |
| | Evenness of external color | Even |
| | Width of band at top devoid of achenes | Small |
| | Yield | Approximate grams per plant: 1,760 g |
| | Firmness | Firm, similar firmness to parent 'Lucia' |
| | % Brix | Seasonal average: 8.9; range 6.4 to 12.5 |

The comparison statistics set forth in the following Tables are with respect to characteristics observed at mid-season of 'Sierra'. All measurements for 'Sierra' were taken at a test plot in Moss Landing, Monterey County, Calif. during mid-season 2020. In Tables 2 and 3, the characteristics of 'Sierra' are compared with historical data of the day neutral variety 'Sweet Ann' (U.S. Plant Pat. No. 22,472) and short-day female parent variety 'Lucia.' Color identifications where noted herein are in accordance with the Panton Color Formula Guide.

PLANTS AND FOLIAGE

The form and structure of the plants of 'Sierra' are slightly smaller than that of 'Lucia' and 'Sweet Ann' plants. The plant spread of 'Sierra,' however, is larger than that of either 'Sweet Ann' or 'Lucia.' The canopy of 'Sierra' is slightly denser than that of 'Sweet Ann,' and more comparable to parent 'Lucia.' The leaf surface of 'Sierra' is also less blistered than that of its parent 'Lucia' and more closely resembling that of 'Sweet Ann.' The glossiness of the leaves of 'Sierra' is also less glossy than that of 'Lucia' and slightly less than that of 'Sweet Ann.' In Table 2, comparative data for foliar characteristics are presented for 'Sierra' and historical data of the two comparison cultivars, 'Sweet Ann' and 'Lucia.'

TABLE 2

| Foliar Characteristics of 'Sierra' Compared to 'Lucia' and 'Sweet Ann' | | | | |
|---|---|---|---|---|
| Foliar | | Cultivar | | |
| Characteristics | | 'Lucia' | 'Sweet Ann' | 'Sierra' |
| Plant height (mm) | Average | 391 | 380 | 352 |
| | Range | 292-490 | 290-480 | 300-410 |
| Plant spread (mm) | Average | 472 | 420 | 511 |
| | Range | 430-550 | 330-510 | 400-600 |
| Leaf width (mm) | Average | 195 | 165 | 352 |
| | Range | 165-220 | 130-195 | 265-385 |
| Mid-tier leaflet length (mm) | Average | 103 | 88 | 91 |
| | Range | 82-116 | 72-105 | 85-100 |
| Mid-tier leaflet width (mm) | Average | 91 | 67 | 80 |
| | Range | 73-102 | 52-88 | 66-88 |
| Petiole length (mm) | Average | 268 | 220 | 266 |
| | Range | 230-355 | 150-280 | 199-300 |
| Petiole diameter (mm) | Average | 4.48 | 3.74 | 4.34 |
| | Range | 3.70-5.80 | 3.01-4.29 | 3.46-5.08 |
| Number leaflets per leaf | | 3 | 3 | 3 |
| Leaf convexity | | Slight concave | Slight concave | slight concave to slight convex |
| Shape leaflet base | | Rounded to obtuse | Obtuse | Rounded to cuneate |
| Leaf pubescence | | Medium density | Medium density | Medium density |
| Petiole pubescence | | Medium density | Medium density | Medium density |
| Stipule length (mm) | Average | 35.74 | Not available | 10.9 |
| | Range | 30.2-39.7 | Not available | 7.15-12.79 |
| Stipule anthocyanin coloration | | Yes | Weak yes | Slight |
| Leaf margins | | Serrate to crenate | Commonly crenate | Serrate to crenate |
| Leaf color adaxial surface | | 364 U | 364 U | 371 C |
| Leaf color abaxial surface | | 363 U | 370 U | 7490 U |
| Petiole color | | 366 U | 383 U | 381 U |
| Leaf surface blistering | | Medium | Very weak | Slight |
| Leaf surface glossiness | | High | Medium | Slight |

FLOWERS AND FRUIT

'Sierra' is a short-day variety that has ever-bearing tendencies under certain temperature and horticultural conditions. This has been seen where plants grown in a coastal climate have continuously flowered throughout the growing season, while in nursery production in Manteca where temperatures are hot, plants do not flower repeatedly. While 'Lucia' has longer inflorescences and 'Sweet Ann' has shorter inflorescences as compared to 'Sierra,' when compared to their individual plant size all three varieties produce flowers that are near or above the canopy level, leaving flowers exposed to pollinators. The light red exterior color of the fruit of 'Sierra' is similar in color to that of 'Lucia' and 'Sweet Ann,' however while 'Sweet Ann' often has an unripe shoulder, no such shoulder exists in fruit of 'Sierra' where it ripens nearly up to the calyx. The fruit of 'Sierra' has good culinary qualities, including great shape, good size, lighter red color, and a great strawberry flavor.

In Table 3, comparative data for flower and fruit characteristics for 'Lucia,' 'Sweet Ann' and 'Sierra' are set forth.

TABLE 3

Flower and Fruit Characteristics of 'Sierra' Compared to 'Lucia' and Sweet Ann'

| Characteristic | | Cultivar | | |
|---|---|---|---|---|
| | | 'Lucia' | 'Sweet Ann' | 'Sierra' |
| Petal number | | 5 | 5-6 | 5-7 |
| Petal length (mm) | Average | 12.44 | 11.21 | 12.9 |
| | Range | 10.6-14.3 | 9.2-13.13 | 8.31-15.99 |
| Petal width (mm) | Average | 11.86 | 11.05 | 11.8 |
| | Range | 10-13.1 | 9.0-13.1 | 8.78-14.67 |
| Position of flower (relative to foliage) | | most exposed | most exposed some even | most exposed some even |
| Pedicel length (mm) | Average | 430 | 330 | 380 |
| | Range | 380-540 | 240-420 | 325-440 |
| Sepal color (adaxial) | | 364 U | 364 U | 370 U |
| Sepal color (abaxial) | | 37 U | 370 U | 392 U |
| Corolla diameter (mm) | Average | 28.18 | 30.34 28.7 | |
| | Range | 23.5-34.2 | 27.03-32.94 | 17.77-34.12 |
| Fruit color (external) | | 1788 C | 185 C | 185 C |
| Fruit color (internal) | | 179 C | 1788 C | 032 U |

Leaf samples from 'Sierra,' along with several proprietary selections from the breeding program including 'Lucia,' 'Emilia', 'Sweet Ann', 'Camila' (U.S. Plant Pat. No. 30,326), 'Ruby June' (U.S. Plant Pat. No. 27,190), 'Sangria (U.S. Plant Pat. No. 30,426), and 'Scarlet' (U.S. Plant Pat. No. 27,034), were submitted to a lab for allelic fingerprint comparison to the over two hundred other varieties of strawberry in its data base. The allelic fingerprint analysis establishes that 'Sierra' is distinct and unique compared to the lab's large database of allelic fingerprints. Table 4 below sets forth the test results of three markers.

TABLE 4

Allelic Fingerprint Analysis

| Cultivar | M1 | M2 | M3 |
|---|---|---|---|
| 'Camila' | 204, 206, 224, 229 | 190, 232 | 279, 281, 289 |
| 'Emilia' | 204, 206, 214, 229 | 190, 232 | 279, 281, 289 |
| 'Lucia' | 202, 204, 206, 229 | 188, 216, 232 | 279, 281, 289 |
| 'Ruby June' | 206, 224, 229 | 188, 190, 216, 232 | 279,289 |
| 'Sangria' | 204, 206, 229 | 190, 216 | 279, 289 |
| 'Scarlet' | 204, 206, 214, 229 | 173, 190, 232 | 279, 281, 289 |
| 'Sweet Ann' | 204, 206, 229 | 190, 216, 232 | 279, 281, 289 |
| 'Sierra' | 204, 206, 229 | 232 | 279, 289 |

We claim:

1. A new and distinct strawberry plant named 'Sierra' as described and illustrated by the characterizations set forth above.

* * * * *